United States Patent [19]

Frank et al.

[11] Patent Number: 4,760,730

[45] Date of Patent: Aug. 2, 1988

[54] CALIBRATION SYSTEM FOR BLOOD PRESSURE TRANSDUCER

[75] Inventors: Thomas P. Frank, Dublin; Jeffrey L. Thompson, Columbus, both of Ohio

[73] Assignee: Medex, Inc., Hilliard, Ohio

[21] Appl. No.: 72,909

[22] Filed: Jul. 14, 1987

[51] Int. Cl.⁴ .................................. G01L 27/00
[52] U.S. Cl. ........................................ 73/4 R
[58] Field of Search ............... 73/1 R, 4 R; 128/672, 128/673, 674, 675; 307/149; 323/367

[56] References Cited

U.S. PATENT DOCUMENTS

| | | | |
|---|---|---|---|
| 3,063,283 | 11/1962 | Polansky | 73/1 R |
| 3,319,155 | 5/1967 | Koolman et al. | 323/367 |
| 3,535,637 | 10/1970 | Goransson | 73/1 R |
| 4,603,574 | 8/1986 | Norman | 73/4 R |
| 4,610,256 | 9/1986 | Wallace | 73/4 R |
| 4,611,601 | 9/1986 | Bowman | 128/673 |
| 4,683,894 | 8/1987 | Kodama et al. | 128/675 |

FOREIGN PATENT DOCUMENTS 0103442  8/1980  Japan ..................... 73/4 R

Primary Examiner—Stewart J. Levy
Assistant Examiner—Robert R. Raevis
Attorney, Agent, or Firm—Wood, Herron & Evans

[57] ABSTRACT

A system for calibrating a blood pressure transducer and monitor combination. The transducer assembly has a calibration resistor. The monitor cable has a housing which contains a switch and a shunt resistor. Electrical connections are provided to place the calibration resistor and shunt resistor in series with each other and in shunt across one leg of a transducer bridge to produce a reading of 100 mmHg on the monitor.

6 Claims, 2 Drawing Sheets

CALIBRATION SYSTEM FOR BLOOD PRESSURE TRANSDUCER

BACKGROUND OF THE INVENTION

This invention relates to apparatus for measuring a physiological pressure, particularly a blood pressure, and more specifically, the invention relates to an electrical calibration system for such blood pressure monitoring apparatus.

In blood pressure monitoring apparatus to which the invention is directed, a catheter is inserted into a patient's blood vessel, the catheter being connected by tubing to a pressure transducer. A saline solution normally fills the tubing between a catheter and the transducer. The liquid in the system applies a pressure, directly related to the patient's blood pressure, to a diaphragm in the transducer. A Wheatstone bridge of four strain gauge resistors is formed on a silicon chip that is connected mechanically or through a fluid to the transducer diaphragm to produce a change in resistance dependent upon the flexing of the diaphragm.

The transducer is connected to a monitor which provides a continuous real time display of variations in the patient's blood pressure as provided by the transducer bridge. Part or all of the transducer is disposable. One form is a completely disposable transducer unit which receives the saline solution in one part and provides the electrical signal from another part. Another form provides a reuseable transducer section and a disposable transducer dome which is mounted on the transducer section. The saline solution which can become contaminated is isolated from the transducer in the reuseable section by a diaphragm mounted on the disposable transducer dome.

Substantially all systems provide for a calibration check. In that check, a resistance is connected, by a switch, across one leg of the bridge transducer in such a fashion that the monitor will show a pressure of 100 mmHg if the electrical connections are proper. In most hospitals where apparatus of this type is used, it is part of the daily or new shift procedure to close that switch to determine whether the apparatus is functioning properly. If there is no reading whatsoever, an open circuit has been introduced into the system. If the reading varies significantly from 100 mmHg, something has happened to cause extraneous resistance to creep into the system.

Many monitors have a switch on the monitor itself by which the shunting resistance is connected across the bridge. U.S. Pat. No. 4,603,574 discloses resistance that is mounted on the cable, as part of the transducer assembly, with series switches provided to make the shunt connection.

SUMMARY OF THE INVENTION

In the present invention, a switch and a calibration resistance are mounted in a housing connected to the reuseable cable that is directly connected to the monitor. The resistance is 150,000 ohms and is to be connected across one leg of bridge transducer. Resistance in addition to the 150K is necessary to produce the 100 mmHg reading. That additional resistance is a calibration resistance which is on the transducer and which is factory-applied and trimmed to accommodate variations in the manufacture of the transducer bridge. Economy is produced by this arrangement in that the transducer and cable assembly including the factory-calibrated resistance are intended to be disposable. The expensive switch and 150K resistor are mounted on the monitor cable, preferably close to the monitor, and are reuseable. Thus, the expense of disposing of a switch and 150K resistor when the transducer is disposed of is avoided.

The present invention is adapted to be used with existing monitor-mounted calibration switches and circuits. Thus, when the present invention is applied to such a monitor, the hospital staff, used to pushing a switch on the monitor for calibration, does not have to learn new procedures. On the other hand, where the monitor has no switch or where it is handier to push the switch on the cable, the system of the present invention redundantly provides for calibration from a switch on the cable.

BRIEF DESCRIPTION OF THE DRAWINGS

As shown in FIG. 1, the apparatus, indicated at 10, includes a transducer 11. A catheter 12 inserted into the arm 13 of a patient is connected by tubing 14 to the fluid side 15 of the transducer 11. A saline solution from a supply 16 is connected by tubing 17 to the fluid side of the transducer 11 and is controlled by a stopcock and flush valve 18. The transducer includes a diaphragm 20 that retains the fluid isolated from the electrical system. The electrical system includes a silicone chip 21 that contains the Wheatstone bridge. Additionally, there are other components such as temperature compensation, null set components and the like forming part of the transducer.

Figure 1:
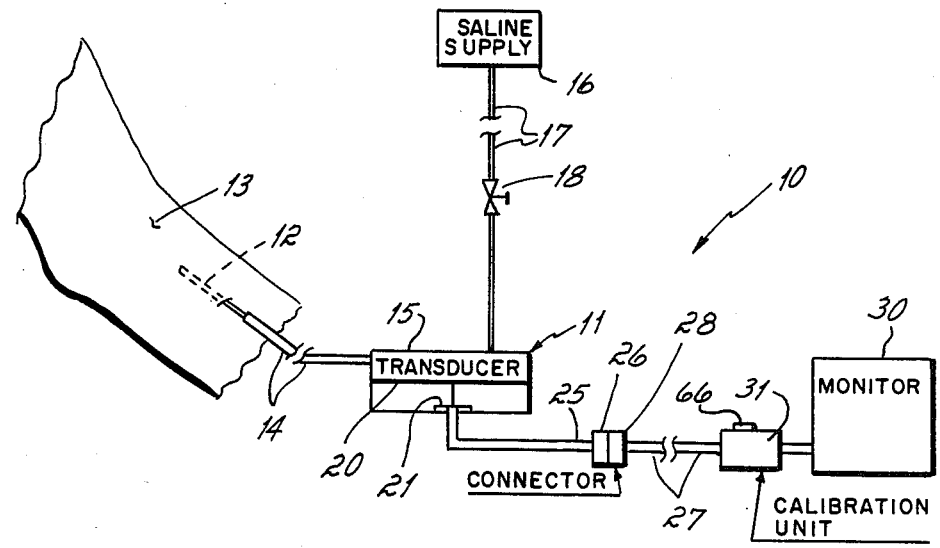
FIG. 1 is a diagrammatic view of a blood pressure monitoring system of the present invention.

The transducer is connected by a short cable pigtail 25 to a multi-contact connector 26. That connector is connected to a monitor cable 27 by a connector 28, and thence to a monitor 30. A calibration unit 31 fixed in the monitor cable 27 contains the shunt resistance or resistances, depending upon the embodiment, that are to be connected in parallel across one leg of the transducer bridge.

Figure 2:
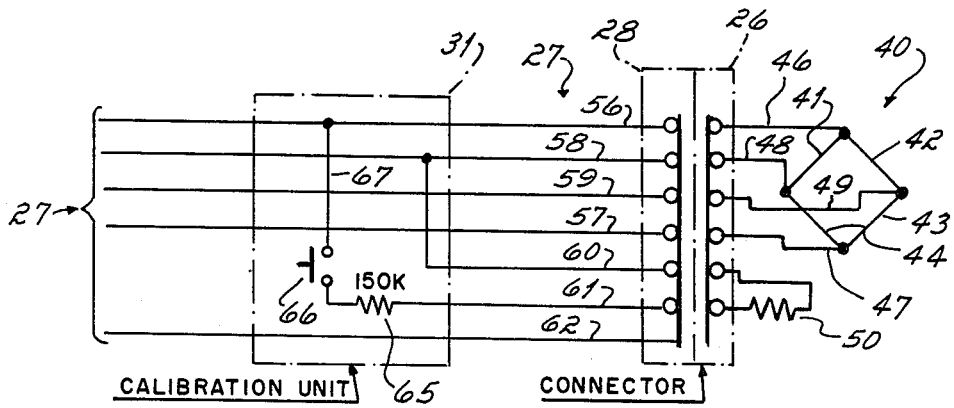
FIG. 2 is a circuit diagram of one embodiment of the invention.

Referring to FIG. 2, a transducer bridge 40 having legs 41, 42, 43 and 44 is shown. Input or excitation leads 46 and 47 are connected to opposed corners of the bridge. Output or signal leads 48 and 49 are connected to the remaining corners of the bridge. These leads form four contacts of the connector 26. A calibration resistor 50 is connected across the two remaining contacts of the connector 26. Resistor 50 is trimmed with respect to the resistances in the bridge so that when it is connected in series with 150K ohm resistance and the two connected across leg 41 of the bridge, the transducer will produce a reading of 100 mmHg at the monitor.

It is to be understood that 150K is an electrical value for the resistance and any other value could be used providing it produces the desired readout of 100 mmHg. (There is nothing critical about 100 mmHg. It is what hospital staffs are used to.) Selection of resistance different than 150K will of course require a change in the resistance of the resistor 50. The monitor cable is shown as providing six leads 56, 57, 58, 59, 60, 61 corresponding to leads 46–49, respectively, as well as two leads 60 and 61 that are connected to the resistor 50. A shield is indicated at 62. The lead 61 is connected to one side of the 150K shunt resistor 65. The other side of that resistor is connected to a switch 66, the switch being connected by a lead 67 to the lead 56. In FIG. 2, the lead 67 is connected to one of the leads to bridge leg 41.

The other lead 60 that is connected to calibration resistance 50 is connected to the lead 58. Thus, when the switch 66 is closed, resistors 50 and 65 are connected in series and that series connection is connected in shunt across the leg 41 of the bridge. When the system is operating properly, that connection will produce a reading of 100 mmHg on the monitor.

Figure 3:
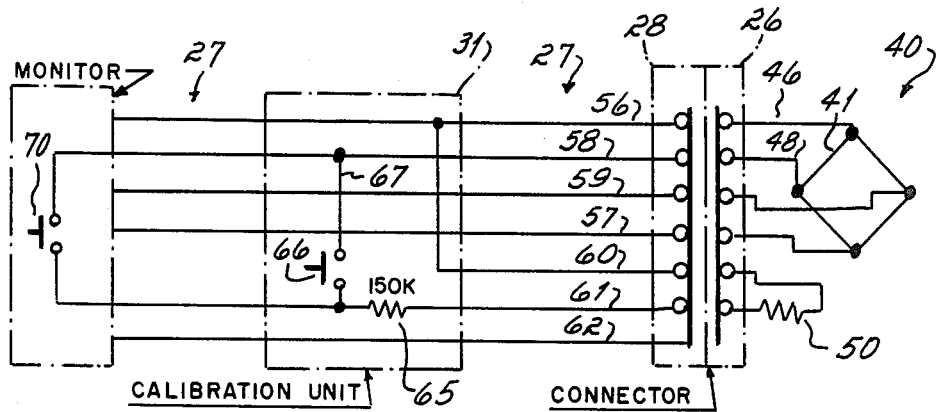
FIGS. 3–5 are circuit diagrams of alternative embodiments of the present invention.

FIG. 3 shows an embodiment where a monitor is equipped with a calibration switch 70. The calibration switch 70 is connected across switch 66 so that the series combination of resistors 50 and 65 can be placed across leg 41 by closing either switch 66 or the monitor-mounted switch 70.

Figure 4:
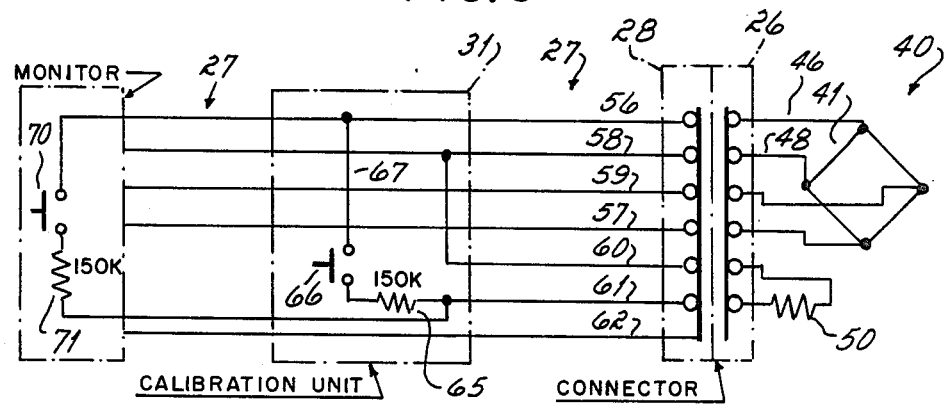

FIG. 4 shows an embodiment in which the monitor contains its own 150K ohm resistance 71. That resistance is connected at one side to the monitor switch 70 and at the other side to a point between the calibration resistance 50 and the shunt resistance 66. With this combination, a calibration check can be made by pushing either switch 66 or switch 70. If switch 66 is pushed, the resistors 50 and 65 are connected across leg 41. If the monitor-mounted switch 70 is closed, the combination of resistor 50 and 71, also 150K, is placed across leg 41 to produce the 100 mmHg.

Figure 5:
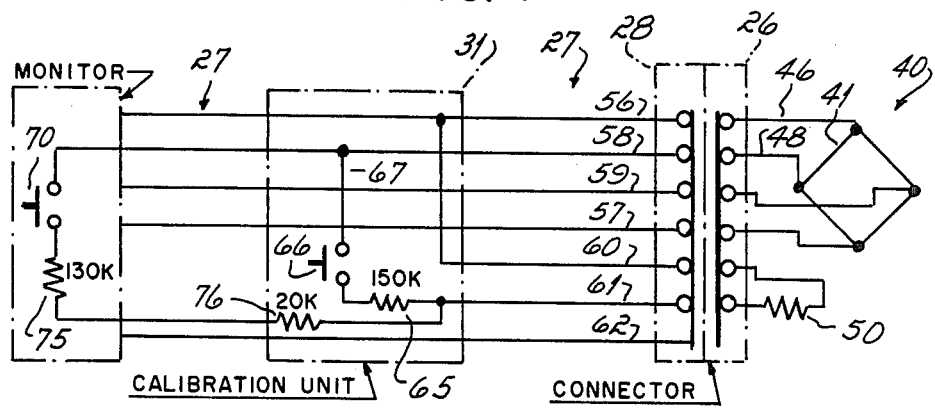

The embodiment of FIG. 5 is similar to the embodiment of FIG. 4 except that the monitor resistance 75 is 130K. 130K, if combined with the calibration resistor 50 and placed across the leg 41, will not produce a 100 mmHg readout. The combined shunting resistance is too low. Accordingly, a supplemental 20K resistance 76 is mounted in the housing 31 and connected in series with the 130K resistance of the monitor. Thus, the combined resistances produce 150K which, when connected in series with calibration resistor 50 and across the leg 41 upon closing monitor switch 70, produces the 100 mmHg readout.

In the operation of its circuits, the blood pressure monitoring system is connected to the patient by inserting the catheter into the blood vessel of the patient and filling the tube 14 with a saline solution as is conventional. Blood pressure from the patient is transmitted through the saline solution to the diaphragm 20 of the transducer. The diaphragm 20 is directly connected by fluid or mechanical connection to the silicon transducer chip 21 and produces an electrical signal that is transmitted to the monitor 30 providing a readout. From time to time a calibration check is made by closing switch 66 that connects the 150K to the calibration resistance 50 across leg 41 of the bridge. That check should produce a 100 mmHg readout so the attendant will know that something is wrong with the system. With the circuits of FIGS. 3–5 in addition to being able to make the check by closing switch 66 on the housing 31, the check can be made by closing the switch 70 on the monitor.

The connections of lead 67 to lead 56 and lead 60 to lead 58 in the embodiments of FIGS. 2 and 4 are reversed in the embodiments shown in FIGS. 3 and 5 where the lead 67 is connected to lead 58 and the lead 60 is connected to lead 56. In either case, the resistance is shunted across bridge leg 41.

There is no electrical difference. The different connections are dictated by the way the monitor switch is connected to the cable leads, as indicated in FIGS. 3–5.

From the above disclosure of the general principles of the present invention and the preceding detailed description of a preferred embodiment, those skilled in the art will readily comprehend the various modifications to which the present invention is susceptible. Therefore, we desire to be limited only by the scope of the following claims and equivalents thereof:

We claim:

1. In a physiological pressure transducing system having a monitor, a transducer assembly including a six contact first connector and bridge-type transducer element having four legs, two excitation leads and two signal leads between said monitor and said bridge, said leads being connected to four of said contacts, a calibration system comprising:
   a factory adjusted calibration resistor mounted on said transducer assembly and connected to the two remaining connector contacts,
   a monitor cable connected to said monitor and having six leads and a second connector for connecting said leads to said six contacts,
   a calibration unit connected in said monitor cable, said unit including
      a shunt resistor having one side connected to one side of said calibration resistor,
      a switch connected between the other side of said shunt resistor and one side of one of said bridge legs,
      and means connecting the other side of said calibration resistor to the other side of said one bridge leg, whereby, closing of said switch connects said calibration and shunt resistors in series across said one bridge leg.

2. A pressure transducing system as in claim 1 in which said monitor has a second shunt resistor and a series-connected switch,
   means connecting one side of said second shunt resistor and switch combination to said one side of said one bridge leg and connecting the other side of said combination to said one side of said calibration resistor.

3. A pressure transducing system as in claim 2 further comprising:
   a supplemental resistance in said unit and means connecting said supplemental resistance in series with said second shunt resistor, the magnitude of said resistance being such that the total of said resistance and second shunt resistor is equal to the magnitude of said first named shunt resistor,
   whereby calibration is effected by closing either of said two switches.

4. A pressure transducing system as in claim 1 in which said monitor has a calibration switch,
   means connecting said monitor calibration switch in parallel across said first named switch, whereby said calibration function can be performed by closing either switch.

5. In a physiological pressure transducing system having a monitor, a transducer assembly including a bridge-type transducer having four legs and means including a monitor cable for connecting said transducer assembly to said monitor, a calibration system comprising:
   a calibration resistor mounted on said transducer assembly, a shunt resistor connected to said monitor cable,
and means on said monitor cable including a switch for connecting said calibration resistor and said shunt resistor in series across a leg of said bridge to produce an output on said monitor equivalent to 100 mmHg of pressure, said monitor cable being separable from said transducer assembly.

6. In a physiological pressure transducer as in claim 5 in which said shunt resistor is 150,000 ohms.

* * * * *